United States Patent
Erkens et al.

(10) Patent No.: US 10,952,939 B2
(45) Date of Patent: *Mar. 23, 2021

(54) PERCARBONATE-CONTAINING BLONDING AGENT IN AN ALUMINUM SACHET

(71) Applicant: Henkel AG & Co. KGaA, Duesseldorf (DE)

(72) Inventors: Udo Erkens, Willich (DE); Torsten Lechner, Langenfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/721,686

(22) Filed: Dec. 19, 2019

(65) Prior Publication Data

US 2020/0206103 A1 Jul. 2, 2020

(30) Foreign Application Priority Data

Dec. 28, 2018 (DE) ...................... 10 2018 133 661.6
Sep. 20, 2019 (DE) ...................... 10 2019 214 384.9

(51) Int. Cl.
| | | |
|---|---|---|
| A61Q 5/08 | (2006.01) | |
| A61K 8/22 | (2006.01) | |
| A61K 8/23 | (2006.01) | |
| A61K 8/19 | (2006.01) | |
| A45D 7/00 | (2006.01) | |

(52) U.S. Cl.
CPC ................ *A61K 8/22* (2013.01); *A61K 8/19* (2013.01); *A61K 8/23* (2013.01); *A61Q 5/08* (2013.01); *A45D 2007/001* (2013.01)

(58) Field of Classification Search
CPC ... A61Q 5/08; A61K 8/22; A61K 8/19; A61K 8/23; A61K 8/46; A61K 8/731; A61K 8/73; A61K 8/26; A61K 2800/48; A61K 8/85; A45D 2007/001
USPC .......................................................... 424/62
See application file for complete search history.

(56) References Cited

U.S. PATENT DOCUMENTS

| | | |
|---|---|---|
| 3,823,231 A | 7/1974 | Bucaria |
| 2011/0232669 A1* | 9/2011 | Suenger .................. A61K 8/44 132/208 |

FOREIGN PATENT DOCUMENTS

| | | |
|---|---|---|
| JP | 2003116632 A | 4/2003 |
| JP | 2018104331 A | 7/2018 |

* cited by examiner

*Primary Examiner* — Eisa B Elhilo
(74) *Attorney, Agent, or Firm* — Lorenz & Kopf, LLP

(57) ABSTRACT

The present disclosure relates to a cosmetic agent for blonding human hair comprising (i) a package comprising at least one multilayer film comprising at least one metal-containing layer as a barrier layer, and (ii) a bleaching agent composition contained in the package, the bleaching agent composition containing at least one percarbonate and at least one inorganic salt of a peroxosulfuric acid. Furthermore, the present disclosure relates to a method for blonding human hair.

20 Claims, No Drawings

PERCARBONATE-CONTAINING BLONDING AGENT IN AN ALUMINUM SACHET

CROSS-REFERENCE TO RELATED APPLICATION

This application claims priority to German Patent Application No. 10 2019 214 384.9, filed Sep. 20, 2019 and to German Patent Application No. 10 2018 133 661.1, filed Dec. 28, 2018, which are both incorporated herein by reference in their entirety.

TECHNICAL FIELD

The present disclosure relates to a cosmetic agent for blonding human hair comprising (i) a package comprising at least one multilayer film comprising at least one metal-containing layer as a barrier layer, and (ii) a bleaching agent composition contained in the package, the bleaching agent composition containing at least one percarbonate and at least one inorganic salt of a peroxosulfuric acid. Furthermore, the present disclosure relates to a method for blonding human hair.

BACKGROUND

The blonding or lightening of one's own hair or generally an oxidative color change has always been the desire of many consumers, since a blond hair color is considered attractive and fashionable in terms of desirability. Various blonding agents having different blonding performance are available in the market for this purpose. The oxidizing agents contained in these products are able to lighten the hair fiber by the oxidative destruction of the hair dye melanin and/or artificial dyes. For a moderate blonding effect, the use of hydrogen peroxide, optionally with the use of ammonia or other alkalizing agents, is sufficient as the oxidizing agent alone. A mixture of hydrogen peroxide and peroxo salts, in particular persulfate salts, is usually used to achieve a stronger blonding effect.

These peroxo salts are usually used in the form of a powder which is mixed with a hydrogen peroxide preparation shortly before use. The use of the combination of hydrogen peroxide and persulfates is associated with several disadvantages. The components hydrogen peroxide and persulfate must thus be packed separately, since they react with each other.

At least two separately packaged components, the persulfate powder and the hydrogen peroxide solution, must therefore be mixed with one another for the preparation of the ready-to-use blonding agent. The user who consumes as sustainably as possible is also increasingly paying attention to the ecological aspects of a product. One goal here also is the economization of packaging material. Products that are used in as concentrated a form as possible, which include only one component and that need only to be optimally mixed with water to produce the application mixture, offer a decisive advantage in terms of the economization packaging material.

Such a package can be produced, for example, by bonding or hot-pressing two plastic films lying one on top of the other, wherein the bonding takes place on all edges of the films. The interior of the package (that is, the plastic bag) produced by bonding can then be filled with the desired cosmetic preparation. The package can be opened by tearing or cutting the plastic bag.

However, the filling of oxidizing agent preparations in such packages is associated with problems whose cause is due to the reactivity of the oxidizing agent. Oxidizing agents are highly reactive, usually liquid or pasty, substances which, depending on the storage conditions and possibly on the presence of decomposing active impurities, decompose in small amounts to form oxygen (that is, gas).

The developer bottles known from the state of the art are usually filled with the oxidizing agent composition at most only one half, usually only one third, of their internal volume. As a rule, developer bottles are made of polyethylene. Since polyethylene is permeable with respect to both water vapor and gases, no or very little overpressure arises in the developer bottle. In addition, developer bottles are usually provided with sturdy, thick walls and a sturdy screw-on closure, so that the diffusion of water vapor or gases through the thickness of the walls is reduced and a slight pressure increase taking place within the bottle has no negative effects.

As a result, the packages are usually bulky, which impairs the sustainability in matters of environmental and resource conservation. An advantage would be provided if a solid was used as an oxidizing agent instead of liquid hydrogen peroxide. The bleaching agent components could then also be offered in a container since the reaction of the components only requires mixing with water.

Persulfates and percarbonates are known as solid oxidizing agents for bleaching agents. They are used as salts, which react under the influence of moisture, which diffuses into packages, and form gases. As a result, packages containing blonding agents can burst.

BRIEF SUMMARY

Cosmetic agents for blonding keratinic fibers, and methods of blonding human hair using the cosmetic agents, are provided herein. In an embodiment, a cosmetic agent for blonding keratinic fibers includes:
(i) a package comprising at least one multilayer film, wherein the multilayer film comprises at least one layer comprising metal as a barrier layer, and
(ii) a bleaching agent composition contained in the package, wherein the bleaching agent composition includes:
  at least one percarbonate in a total amount of from about 2 to about 14% by weight based on the total weight of the bleaching agent composition and
  at least one inorganic salt of a peroxosulfuric acid, in a total amount of from about 10 to about 70% by weight based on the total weight of the bleaching agent composition.
The metal of the layer containing metal includes aluminum.

In another embodiment, a cosmetic agent for blonding keratinic fibers includes:
(i) a package comprising at least one multilayer film, wherein the multilayer film comprises at least one layer comprising metal as a barrier layer, and
(ii) a bleaching agent composition contained in the package, wherein the bleaching agent composition includes:
  an alkali metal, alkaline earth metal or ammonium salt of a percarbonate in a total amount of from about 6 to about 12% by weight based on the total weight of the bleaching agent composition; and
  a mixture of potassium peroxodisulfate, ammonium peroxodisulfate, and sodium peroxodisulfate in a total amount of from about 30 to about 50% by weight based on the total weight of the bleaching agent composition. The metal of the layer containing metal includes aluminum.

In another embodiment, a method of blonding human hair is provided in which
(a) the cosmetic agent as described above is introduced into an amount of water,
(b) the resulting mixture from (a) is homogenized, and
(c) the mixture homogenized from (b) is applied to human hair.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present application is to provide a cosmetic bleaching composition which can be packaged in less packaging material in a space-saving and safe manner, without having to put up with disadvantages in handling. Furthermore, the cosmetic bleaching composition should be packaged so that the mechanical strength of the package is sufficiently large, with safe and space-saving storage being made possible, wherein easy accessibility to the ingredients is to be guaranteed.

The problem underlying the present disclosure is solved by the cosmetic agents as contemplated herein. A first subject of the present disclosure is therefore a cosmetic agent for blonding keratinic fibers, in particular human hair, comprising
(i) a package comprising at least one multilayer film comprising at least one metal-containing layer as a barrier layer, and
(ii) a bleaching agent composition, contained in the package, exemplified in that the bleaching agent composition contains at least one percarbonate in a total amount of from about 2 to about 14% by weight, preferably from about 6 to about 12% by weight, more preferably from about 8 to about 10% by weight, based on the total weight of the bleaching agent composition and at least one inorganic salt of a peroxosulfuric acid, in a total amount of from about 10 to about 70% by weight, more preferably from about 20 to about 50% by weight, yet more preferably from about 25 to about 45% by weight, most preferably from about 30 to about 40% by weight, each based on the total weight of the bleaching agent composition, wherein the metal of the metal-containing layer comprises aluminum.

Keratinic fibers, keratin-containing fibers or keratin fibers are understood to mean furs, wool, feathers and, in particular, human hair. Although the agents as contemplated herein are primarily suitable for lightening keratin fibers, in principle, there is nothing to prevent their use in other fields as well.

The product as contemplated herein is a product for the oxidative color change of keratinic fibers, that is, a product which is applied to the human head to achieve oxidative lightening or shading of the hair. In this context, shading is understood to mean a dyeing in which the color result is lighter than the original hair color.

The cosmetic product as contemplated herein comprises, as a first component, a package (VP) which comprises at least one multilayer film (F). This film contains at least one first polymer layer (P1), at least one second polymer layer (P2) and at least one barrier layer (BS). This multilayer film constitutes the wall or the outer shell of the package. As described above, such a package is usually made by gluing, pressing or sealing two superimposed pieces of film (wherein the package (VP) is filled simultaneously with the bleaching agent composition), that is, such a package is closed at all edges. This package can be opened, for example, by tearing or cutting open.

As contemplated herein, the metal-containing layer of the film of the package comprises aluminum. This ensures that moisture cannot diffuse into the interior of the package. Thus, no gases which cause inflation of the package are formed.

The thickness of the multilayer film (F) should in this case be designed so that a sufficient mechanical stability is present, but at the same time, the film (F), and thus the package produced from the film (VP), is so flexible that a complete removal the bleaching agent composition from the opened package (VP) by pressing together or pressing is enabled. These requirements are met in particular when the film (F) has a certain total thickness. Preferred embodiments of the present disclosure are therefore exemplified in that the at least one multilayer film has a total thickness of from about 21 µm to about 2.0 mm, preferably from about 30 µm to about 1.0 mm, more preferably from about 50 µm to about 500 µm, in particular from about 60 µm to about 200 µm. For the purposes of the present disclosure, the total thickness of the film (F) is understood to mean the sum of the thicknesses of all the individual layers of the film (F).

Furthermore, the term "package" as contemplated herein is understood to mean a package which is preferably present in the form of a sachet. In a particular embodiment described below, the package can also be a double sachet. A sachet (pouch) is a small package in bag or pouch form, which is often used in the packaging of cosmetics. The capacity of the package, in particular of the sachet, can be, for example, from about 5 to about 1000 ml, preferably from about 10 to about 200 ml and particularly preferably from about 20 to about 50 ml.

A double sachet is a sachet that has two separate chambers. Even the portioning in a double sachet is more space-saving than the portioning of hydrogen peroxide in a plastic bottle. The handling of the bleaching agent composition is greatly simplified by using a double sachet. The percarbonate can be contained in one chamber, the inorganic salt of peroxosulfuric acid can be contained in the other chamber.

The provision of the cosmetic product in the form of a double sachet offers the advantage of space-saving storage and easier handling. The sachet or double sachet can be easily ripped open and mixed with water to obtain a ready-to-use product.

Percarbonates and salts of peroxosulfuric acid, which are suitable for blonding agents, are regularly solids. Preferably, the percarbonate and the salt of peroxosulfuric acid, which are used in the cosmetic agent as contemplated herein, are solids, in particular powdery solids. By containing the bleaching agent composition in the package, it is ensured that the bleaching agent composition is easy to handle and safely dosable. The percarbonate used and the salt of peroxosulfuric acid used do not dust since they are contained in the package in the closed chamber. The package thus forms a closed chamber in the cosmetic agent as contemplated herein. This can be ensured by sealing or gluing the chamber after the bleaching agent composition has been added to the package.

The cosmetic agent as contemplated herein is used for the oxidative lightening of human hair. The term "oxidative lightening" is understood to mean blonding agents and also agents for lightening the keratin fibers which contain the percarbonate and the salt of peroxosulfuric acid. When a pure blonding or lightening is to take place, the cosmetic agents then contain no further dyes. However, it can also be desired to perform a shading of the keratin fibers, in addition to the blonding/lightening. For the purpose of shading, the cosmetic agents as contemplated herein can additionally also contain coloring components such as substantive dyes and/or oxidation dye precursors. However, the preferred use of the cosmetic agents is blonding or lightening, therefore, the cosmetic agents preferably contain either no dyes or these only in small, suitable for amounts for easy shading.

The bleaching agent composition contains at least one percarbonate as a first component. This serves as contemplated herein as a replacement for hydrogen peroxide. Hydrogen peroxide is produced for bleaching the hair by blending the components of the bleaching agent composition comprising the percarbonate.

According to a preferred embodiment of the present disclosure, cosmetic agents contain a bleaching agent composition in which the at least one percarbonate constitutes an alkali metal, alkaline earth metal or ammonium salt of a percarbonate, in particular sodium percarbonate.

As contemplated herein, the at least one percarbonate, in particular sodium percarbonate, is present in the bleaching agent composition in a total amount of from about 2 to about 14% by weight, preferably from about 6 to about 12% by weight, based on the total weight of the bleaching agent composition. This achieves the best results in terms of complete replacement of liquid hydrogen peroxide as the oxidizing agent.

A percarbonate should preferably be understood to mean an $H_2O_2$ adduct. Sodium percarbonate in the context of the present disclosure is understood to mean the adduct (or complex) of sodium carbonate and hydrogen peroxide having the composition $2Na_2CO_3 \times 3H_2O_2$. Sodium percarbonate forms a white, water-soluble powder which, when in contact with water, formally decomposes into sodium carbonate and hydrogen peroxide. The sodium percarbonate as contemplated herein ($2Na_2CO_3 \times 3H_2O_2$) has a molar mass of 314.02 g/mol and has the CAS number 15630-89-4.

Sodium percarbonate is commercially available from a variety of suppliers at various degrees of purity. For example, Evonik Degussa offers a sodium percarbonate having a purity of 98.8% by weight. All of the aforementioned quantities are based on about 100% sodium percarbonate. The quantities to be used must be converted accordingly when using sodium percarbonate in lower degrees of purity.

Analogously, potassium percarbonate in the context of the present disclosure is understood to mean the adduct (or complex) of potassium carbonate and hydrogen peroxide having the composition $2K_2CO_3 \times 3H_2O_2$.

The use of sodium percarbonate has been found to be particularly suitable for achieving the object of the present disclosure.

It has been found that the hair damage could be reduced when smaller amounts of percarbonates were used in the cosmetics than conventionally used. The work leading to this present disclosure has shown that further increasing the amount of percarbonate beyond about 14% by weight increases hair damage but does not result in further enhancement of the lightening. It has been found to be more preferable in this connection to use the percarbonate in the preferred quantitative ranges. The best brightening performance with comparatively least damage to the hair could be obtained when the cosmetic agents contained the percarbonates (especially sodium percarbonate) in a total amount of from about 6 to about 12% by weight.

All figures in % by weight in the context of the present disclosure refer to the total weight of the bleaching agent composition or to the total weight of components in the various chambers (in the case of double-chamber sachets), as indicated. When a mixture of sodium percarbonate and potassium percarbonate is used, the data in % by weight of course is the sum of the weight percentages. The same naturally applies analogously to the salts of peroxosulfuric acid.

The cosmetic agent in the bleaching agent composition contains at least one salt of peroxosulfuric acid as a second component of the bleaching agent composition essential to the present disclosure. Peroxosulfuric acids are understood to mean peroxodisulfuric acid and peroxomonosulfuric acid (Caro's acid).

According to a preferred embodiment of the present disclosure, the at least one inorganic salt of a peroxosulfuric acid is selected from the group of sodium peroxodisulfate, potassium peroxodisulfate, ammonium peroxodisulfate, sodium peroxomonosulfate, potassium peroxomonosulfate and ammonium peroxomonosulfate. Or the inorganic salt of a peroxosulfuric acid comprises mixtures of said inorganic salts of a peroxosulfuric acid, preferably mixtures of potassium peroxodisulfate and ammonium peroxodisulfate or mixtures of sodium peroxodisulfate and ammonium peroxodisulfate.

According to the present disclosure, the total amount of inorganic salt of a peroxosulfuric acid is from about 10 to about 70% by weight, more preferably from about 20 to about 50% by weight, still more preferably from about 25 to about 45% by weight, most preferably from about 30 to about 40% by weight, in each case based on the total weight of the blonding agent. This has proven to be beneficial for the blonding effect.

According to a particularly preferred embodiment of the present disclosure, the inorganic salt of a peroxosulfuric acid constitutes a mixture comprising from about 5 to about 40% by weight, preferably from about 10 to about 35% by weight, more preferably from about 15 to about 30% by weight of potassium peroxodisulfate, from about 5 to about 20% by weight, preferably from about 8 to about 18% by weight, more preferably from about 10 to about 15% by weight of ammonium peroxodisulfate and from 0 to about 10% by weight, preferably from about 1 to about 9% by weight, more preferably from about 2 to about 6% by weight if sodium peroxodisulfate, in each case based on the total weight of the blonding agent.

Ammonium persulfate is alternatively referred to as ammonium peroxodisulfate and has the empirical formula $(NH_4)_2S_2O_8$. Ammonium persulphate has the CAS number 7727-54-0. Potassium persulfate is alternatively referred to as potassium peroxodisulfate and has the empirical formula $K_2S_2O_8$. Potassium persulfate has the CAS number 7727-21-1. Sodium persulfate is alternatively referred to as sodium peroxodisulfate and has the empirical formula $Na_2S_2O_8$. Sodium persulfate has the CAS number 7775-27-1.

The salts of peroxosulfuric acid are preferably used in certain total amounts in the cosmetic agent as contemplated herein, in order to optimize both the lightening performance and to minimize hair damage.

The bleaching agent composition can advantageously contain a thickening agent. In the context of the present disclosure, the term "thickening agent" is to be understood to mean compounds which can bind liquids, in particular water, and increase the viscosity of these liquids. In the context of the present disclosure, these also include gelling agents which are capable of thickening liquids to compositions having a gelatinous consistency or to gels. "Thickening agent" and "thickener" are used synonymously in the context of the present disclosure. As contemplated herein, gel-like cosmetic agents or gels are understood to mean dimensionally stable, easily deformable disperse systems of at least two components, the gelling agent (usually a solid, colloidally divided substance having long or highly branched compounds) and a liquid (usually water) as a dispersion agent. The gelling agent forms a spatial network in the liquid, wherein the individual gel-forming compounds adhere to one another by main and/or minor valences at different spatial points.

According to a preferred embodiment of the present disclosure, the at least one thickening agent is a polysaccharide, preferably a mixture of at least two different polysaccharides, more preferably a mixture of an at least partially ionic polysaccharide and a substantially non-ionic polysaccharide.

It has proved, as described above, a special challenge to prepare a cosmetic agent for lightening hair which uses solid substances as the oxidizing agent and no liquid hydrogen peroxide as a component and which at the same time comprises a thickener which advantageously adjusts the viscosity of the ready-to-use cosmetic composition. The problem is that thickening agents, which constitute polyelectrolytes, lose their viscosity-increasing properties with increasing salt content. It has proved to be particularly advantageous when a mixture of two different polysaccharides is used as a thickening agent.

According to a preferred embodiment of the present disclosure, the at least one thickening agent is present in the bleach composition in a total amount of from about 0.5 to about 15% by weight, preferably from about 1 to about 10% by weight, more preferably from about 4 to about 8% by weight, based on the total weight of the bleaching agent composition.

Intensive investigations have surprisingly shown that a mixture of three thickening agents is particularly well suited to achieve the advantageous effect in terms of viscosity. A particularly preferred embodiment of the present disclosure is therefore a cosmetic product in which the at least one thickening agent is a mixture of a cellulose gum, a hydroxyethyl cellulose and a xanthan gum, wherein preferably the amount of cellulose gum is from about 0.2 to about 5% by weight, preferably from about 0.5 to about 3% by weight, the amount of xanthan gum is from about 0.1 to about 5% by weight, preferably from about 0.5 to about 2% by weight, and/or the amount of hydroxyethyl cellulose is from about 0.2 to about 5% by weight, preferably from about 0.5 to about 4% by weight, in each case based on the total weight bleaching agent composition.

In the context of the present disclosure, the use of xanthan, which has a mean particle diameter D50 of from about 140 to about 200 μm and a viscosity (0.3% by weight solution in 0.3% KCl) of from about 250 to about 800 mPas (measured with Brookfield viscometer at 3 rpm) has been shown to be particularly advantageous. Such xanthans are commercially available, for example, under the trade name Keltrol CG-SFT from CP Kelco.

As contemplated herein, the term "xanthans" is understood to mean naturally occurring polysaccharides which can be obtained from sugar-containing substrates with the aid of bacteria of the genus *Xanthomonas*. The xanthan gum d-glucose, d-mannose, d-glucuronic acid, acetate and pyruvate used as contemplated herein preferably contains a molar ratio of 28:30:20:17:5.1-6.3, wherein the main chain includes 0-1,4-linked glucose units (also referred to as a cellulose chain). The xanthans used with particular preference in the context of the present disclosure have the CAS No. 11138-66-2 and the following structural formula

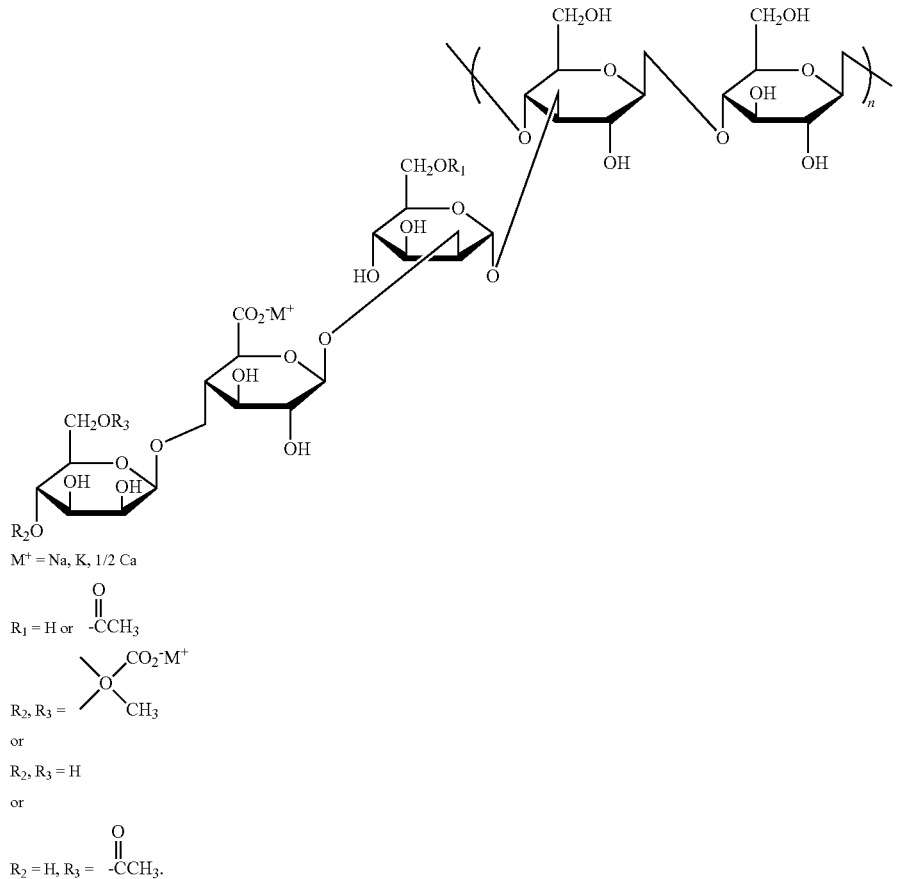

Xanthan by its structure constitutes a polyelectrolyte. The further special thickening agents cellulose gum (carboxymethyl cellulose) and hydroxyethyl cellulose are commercially available under the product names Cekol 5000 or Tylose H 100000 YP2. The hydroxyethylcellulose is a cellulose ether and substantially does not contain any free acid groups.

In the course of the work leading to this present disclosure, it has been found that by using the components essential to the present disclosure, the bleaching agent composition in the special package (VP) comprising a layer containing aluminum can be assembled and stored without this package, which has a barrier layer having a passage blocking effect for gases and water vapor, inflating or bursting. These cosmetic agents can also be handled particularly advantageously. The aluminum layer is the optimal vapor barrier.

According to a preferred embodiment of the present disclosure, the cosmetic agent is free of hydrogen peroxide. By this is meant that the cosmetic agent is substantially free of hydrogen peroxide, in particular that no hydrogen peroxide is added to the bleaching agent composition during manufacture. Of course, traces of water can be present in the cosmetic agent, which traces produce hydrogen peroxide upon reaction with the percarbonate. However, this should only result in a small amount of free hydrogen peroxide. Hydrogen peroxide can of course also be present formally in the empirical formula of the solid oxidizing agent, in the crystal structure of the percarbonate. It is thus also not available as free hydrogen peroxide.

According to a preferred embodiment of the present disclosure, there is provided a cosmetic agent in which the package constitutes a one-chamber sachet in which the components of the bleaching agent composition are present. In this embodiment, it is a product that is particularly easy to handle. It has surprisingly been found that the combination of the multilayer film, the percarbonate and the inorganic salt of a peroxosulfuric acid together with the thickener completely solves the problem underlying the present disclosure.

Alternatively, the package can be a two-chamber bag in which the percarbonate is contained in a first chamber of the two-chamber bag and the inorganic salt of a peroxosulfuric acid is contained in a second chamber of the two-chamber bag, wherein preferably the multilayer film (F) has an oxygen transmission rate (OTR) at 23° C. and 0% relative humidity of less than about 0.1 cc/m$^2$/d/bar, and has a water vapor transmission at 38° C. and 90% relative humidity of less than about 0.1 g/m$^2$d.

According to a preferred embodiment of the present disclosure, cosmetic agents can be one in which the multilayer film comprises at least one first polymer layer (P1), at least one second polymer layer (P2) and the barrier layer (BS), wherein the first polymer layer (P1) is formed from polyethylene terephthalate or polyethylene naphthalate, in particular from polyethylene terephthalate; the second polymer layer (P2) is formed from a polyolefin, in particular polyethylene; and/or the layer containing metal is formed from aluminum; wherein preferably the first polymer layer (P1) has a layer thickness of from about 5 to about 20 µm, preferably from about 8 to about 16, more preferably from about 10 to about 14 µm; the second polymer layer preferably has a layer thickness of from about 50 to about 100 µm, preferably from about 60 to about 90 µm, more preferably from about 70 to about 80 µm; and preferably, the layer containing metal has a layer thickness of from about 3 to about 30 µm, preferably from about 5 to about 15 µm, more preferably from about 8 to about 12 µm.

According to a preferred embodiment of the present disclosure, there is provided a cosmetic agent wherein the barrier layer (BS) is arranged between the first polymer layer (P1) and the second polymer layer (P2) and/or wherein the first polymer layer is located on the side facing away from the bleaching agent composition. By this it is meant that the first polymer layer lies on the outside and the second polymer layer lies on the inside, that is, it is turned towards the agent.

According to a preferred embodiment of the present disclosure, there is provided a cosmetic agent in which the package constitutes a one-chamber sachet in which the percarbonate and the inorganic salt of a peroxosulfuric acid are present; or exemplified in that the package is a two-chamber bag and the percarbonate is contained in a first chamber of the two-chamber bag and the inorganic salt of a peroxosulfuric acid is contained in a second chamber of the two-chamber bag, wherein preferably the multilayer film (F) has an oxygen transmission rate (OTR) at 23° C. and 0% relative humidity of less than about 0.1 cc/m2/d/bar, and has a water vapor transmission at 38° C. and 90% relative humidity of less than about 0.1 g/m2d. The thickening agent can be contained in the first and/or second chambers in these preferred embodiments.

According to a preferred embodiment of the present disclosure, there is provided a cosmetic agent in which the two-chamber bag comprises a first multilayer film (F1) forming the package of the first chamber and a second multilayer film (F2) forming the package of the second chamber, wherein the oxygen transmission rate (OTR) and the water vapor transmission of the first multilayer film (F1) are different from the oxygen transmission rate (OTR) and the water vapor transmission of the second multilayer film (F2); wherein the first multilayer film (F1) has an oxygen transmission rate (OTR) at 23° C. and 0% relative humidity of from about 0.1 to about 5 cc/m$^2$/d/bar, preferably from about 0.2 to about 3.5 cc/m$^2$/d/bar, more preferably from about 0.5 to about 2.5 cc/m$^2$/d/bar, and a water vapor transmission at 38° C. and 90% relative humidity from about 0.1 to about 5 g/m$^2$d, preferably from about 0.2 to about 3.5 g/m$^2$d, more preferably from about 0.5 to about 2.5 g/m$^2$d, and the second multilayer film (F2) has an oxygen transmission rate (OTR) at 23° C. and 0% relative humidity from about 0.01 to about 0.1 cc/m$^2$/d/bar, preferably from about 0.02 to about 0.09 cc/m$^2$/d/bar, more preferably from about 0.05 to about 0.08 cc/m$^2$/d/bar, and a water vapor transmission at 38° C. and 90% relative humidity of from about 0.01 to about 0.1 g/m$^2$d, preferably from about 0.02 to about 0.09 g/m$^2$d, more preferably from about 0.05 to about 0.08 g/m$^2$d.

This preferred embodiment is to be understood that in the case where the two-chamber bag is formed of two different films, the second multilayer film (F2) has an oxygen transmission rate (OTR) and a water vapor transmission equal to or less than the oxygen transmission rate (OTR) and the water vapor transmission of the multilayer film (F) when the package is formed from only a multilayer film (F). The advantage of this preferred embodiment lies in the adaptation of oxygen transmission rate (OTR) and water vapor transmission as a function of the content. The composition containing peroxide is to be stored differently than the percarbonate composition in particular in terms of oxygen transmission, and the percarbonate composition is to be stored differently than the persulfate composition due to the pH values in term of water vapor transmission. The transmission parameters can be set by the thickness of the barrier layer (BS). A two-chamber bag according to this preferred embodiment can be produced in such a way that the edges of the two chambers are superimposed and glued in the circumference of the surface of each edge sealing seam. Other manufacturing methods are also conceivable.

In addition, a multilayer film (F) in the context of the present disclosure is understood to mean a thin, laminar and windable web of the at least one polymer layer (P1) and the at least one polymer layer (P2). This multilayer film (F) forms the wall of the package (VP). The polymer layers (P1) and (P2) preferably comprise polymers capable of forming films. Furthermore, the polymer layers (P1) and (P2) are preferably polymer layers different from each other. The package additionally contains a barrier layer (BS) which prevents or reduces the passage of water vapor and other gases, such as oxygen, thus preventing or reducing the diffusion of these gases through the wall of the package.

As contemplated herein, the permeability values of the film (F) are advantageously adjusted. The film (F) thus gives the package advantageous barrier properties, in particular with regard to the permeability to water vapor (Water Vapor Transmission Rate; WVTR; measured in units of $g/(m^2 d)$ or $g/(m^2 24\ h)$) measured by the method ASTM E 398 at 38° C. ambient temperature and 90% relative humidity, and for oxygen (Oxygen Transmission Rate; OTR, measured in $cm^3/(m^2 d\ bar)$ or $cm^3/(m^2 24\ h)$—wherein $cm^3$ is equivalent to cc—at an atmospheric pressure of 1 bar) measured by the method ASTM D 3985 at 23° C. ambient temperature and 0% relative humidity.

According to a preferred embodiment of the present disclosure, the first chamber and the second chamber of the double-chamber sachet are separated from one another by at least one sealed seam and the two-chamber bag is provided with a perforation, the separation of which opens both chambers of the two-chamber bag. When the perforation is cut through, an opening is created in each chamber, through which opening the contents of the first chamber and the contents of the second chamber can emerge. The feature according to which the two chambers of the two-chamber bag should be "at least" separated by a sealed seam, is intended to mean that further features can be realized between the bags, for example, there can be a perforation along the sealed seam, the separation of which separates the two bags of the two-chamber bag. Alternatively, the separation of the two chambers can be provided by a film. In the case where the double sachet appears like a simple sachet from the external point of view, wherein the chambers are present only separated by the film or optionally by a double film, the separating film or separating double film is arranged between the two outer films.

The arrangement of the layers (P1), (P2) and (BS) within the multilayer film (F) can be different. Furthermore, it is also possible for the film (F) to comprise further layers in addition to the previously mentioned layers. In addition, it is advantageous as contemplated herein when all of the previously mentioned layers are each oriented parallel to the surfaces of the film (F), that is, all layers have the same orientation.

It is particularly preferred as contemplated herein when the barrier layer (BS) is arranged on the side coming in contact with the bleaching agent composition. The first polymer layer (P1) thus adjoins firstly the barrier layer (BS) and secondly the second polymer layer (P2), which is located on the outside of the package. The polymer layer (P1) here is different from the polymer layer (P2). Here, the barrier layer (BS) serves as a carrier layer, to which then first polymer layer (P1) is then applied. The second polymer layer (P2) is then applied to this polymer layer (P1). The three layers (BS), (P1) and (P2) together form a film (F) whose total thickness is preferably from about 30 μm to about 1.0 mm.

However, in the context of the present disclosure, an arrangement in which the barrier layer (BS) lies between the first polymer layer (P1) and the second polymer layer (P2) is particularly preferred. In this case, the multilayer film (F) includes three layers, wherein the layer (P1) lies in the innermost contact with the bleaching agent composition. The layer (P1) is in contact with the barrier layer (BS), and the barrier layer (BS) in turn makes contact with the layer (P2). In this layer, the layers (P1) and (P2) do not adjoin one another but rather are separated by the barrier layer (BS). In this arrangement, the layers (P1) and (P2) can in principle be made of the same polymeric material, but it is preferred when the two layers (P1) and (P2) are made of different polymeric materials. The three layers (BS), (P1) and (P2) together form a film (F) whose total thickness is preferably from about 30 μm to about 1.0 mm. The particular advantage of this arrangement is that the, often very thin, barrier layer (BS) is located neither on the inner nor on the outer surface of the multilayer film (F), but rather is protected in the direction of the inside through the polymeric layer (P1) and in the direction of the outside by the polymeric layer (P2). In this way, in this arrangement, a mechanical abrasion or mechanical destruction of the barrier layer (BS) is best avoided. It is therefore advantageous in the context of the present disclosure for the at least one multilayer film (F) to contain the at least one barrier layer (BS) between the at least one first polymer layer (P1) and the at least one second polymer layer (P2). The use of such packages has been found to be particularly advantageous in terms of increased storage stability since this arrangement exhibits neither swelling nor delamination with prolonged contact time with an oxidizing agent-containing composition.

Also particularly preferred as contemplated herein is a film (F) in which the first polymer layer (P1) is arranged on the side coming in contact with the bleaching agent composition. The second polymer layer (P2) adjoins the polymer layer (P1) and is different from this. The barrier layer (BS) is located outside. For films (F) with this layering, for example, the layer (P1) can function as a polymeric carrier layer onto which the second polymeric layer (P2) is then applied. Subsequently, the side adjacent to (P2) (that is, the outside) is provided with the barrier layer. It is therefore advantageous in the context of the present disclosure for the at least one multilayer film (F) to contain the at least one barrier layer (BS) on the outside of the package (VP). As contemplated herein, the outside of the package (VP) is understood to mean that side of the package which does not come into contact with the bleaching agent composition, but rather with the environment. The three layers (P1), (P2) and (BS) in this case form a film (F) whose total thickness is preferably from about 30 μm to about 1.0 mm. The use of such packages has been found to be particularly advantageous in terms of increased storage stability since this arrangement exhibits neither swelling nor delamination with prolonged contact time with an oxidizing agent-containing composition.

When the multilayer film (F) contains the above-described three layers (P1), (P2) and (BS), suitable arrangements as contemplated herein of the layers are described below (considered from interior (in contact with the bleaching agent composition)) to the outside):

a) *Interior*-layer (P1)-layer (P2)-barrier layer (BS)-*outside*,
b) *Interior*-layer (P1)-barrier layer (BS)-layer (P2)-*outside*,
c) *Interior*-layer (P2)-layer (P1)-barrier layer (BS)-*outside*,
d) *Interior*-layer (P2)-barrier layer (BS)-layer (P1)-*outside*,
e) *Interior*-barrier layer (BS)-layer (P1)-layer (P2)-*outside*,
f) *Interior*-barrier layer (BS)-layer (P2)-layer (P1)-*outside*, The first polymeric material of the first layer (P1) is as contemplated herein an organic polymeric material. This material can be a polymer type layer or a polymer blend layer. This first layer (P1) can, for example, function as a polymeric carrier material, that is, in the production of the film, a layer or a film of the polymeric material (P1) can be initially furnished and then sprayed, laminated or coated with the further layers as contemplated herein. Preferred embodiments of the present disclosure are exemplified in that the at least one first polymer layer (P1) is formed from polypropylene, polyethylene, polyester, polyamide or polyvinyl alcohol, in particular from polypropylene. The term "is formed" is understood as contemplated herein to mean that the polymer layer contains at least about 70% by weight, preferably at least about 80% by weight, preferably at least about 90% by weight, in particular at least about 99% by weight, each based on the total weight the polymer layer (P1), of the previously mentioned compounds.

A particularly preferred product as contemplated herein is therefore exemplified in that the multilayer film (F) comprises at least one first polymer layer (P1) which is formed from polypropylene. Polypropylene is alternatively referred to as poly(1-methylethylene), and is a thermoplastic polymer which belongs to the group of polyolefins. Polypropylene is made by polymerizing propylene (propene) using various catalysts. For example, polypropylene can be produced by stereospecific polymerization of propylene in the gas phase or in suspension according to Giulio Natta. Polypropylenes as contemplated herein can be isotactic and thus highly crystalline, but also syndiotactic or amorphous. The regulation of the average relative molar mass can be effected, for example, by setting a specific hydrogen partial pressure during the polymerization of the propene. For example, polypropylene can have average relative molecular weights of from about 150,000 to about 1,500,000 g/mol. Polypropylene can be processed, for example, by extrusion and stretch blow molding, or by pressing, calendering, thermoforming and cold forming.

The first polymer layer (P1) preferably has a specific layer thickness. It is therefore preferred in the context of the present disclosure when the at least one first polymer layer (P1) has a layer thickness of from about 20.0 µm to about 300 µm, preferably from about 40.0 µm to about 200 µm, more preferably from about 50.0 µm to about 100 µm, in particular from about 60.0 µm to about 90.0 µm.

A particularly preferred product as contemplated herein is therefore exemplified in that multilayer film (F) comprises at least one first polymer layer (P1), which is formed from polypropylene and has a layer thickness of from about 60.0 to about 90.0 µm.

Furthermore, the multilayer film (F) from which the package is made comprises a second polymer layer (P2) of a second polymeric material. The second polymeric material can be a polymer type layer or a polymer blend layer. In the production of the multilayer film, for example, the second layer (P2) can be sprayed, applied or coated either before or after application of the barrier layer (BS) to the first polymer layer (P1) acting as the carrier layer. However, it is also conceivable that the second polymer layer (P2) acts as a carrier layer, to which the barrier layer (BS) and the first polymer layer (P1) are then applied.

Depending on the sequence of layering described above, the first polymeric material of the first polymer layer (P1) and the second polymeric material of the second polymer layer (P2) can either be the same (when both layers are not in contact with each other) or can be different. The polymer layer (P2) can therefore be formed from the compounds previously mentioned in connection with the polymer layer (P1). Preferably, the layers (P1) and (P2) are made of different polymeric materials (that is, different polymers or polymer blends). It is therefore preferred within the context of the present disclosure for the at least one second polymer layer (P2) to be formed from polyethylene terephthalate or polyethylene naphthalate, in particular from polyethylene terephthalate. The term "is formed" is understood as contemplated herein to mean that the polymer layer contains at least about 70% by weight, preferably at least about 80% by weight, preferably at least about 90% by weight, in particular at least about 99% by weight, each based on the total weight the polymer layer (P2), of the previously mentioned compounds. Polyethylene terephthalate (PET) is a polymer from the group of polyesters. The preparation of polyethylene terephthalate can be carried out, for example, by transesterification of dimethyl terephthalate with ethylene glycol at higher temperatures. Methanol is split off in this transesterification reaction, which is removed by distillation. The resulting bis(2-hydroxyethyl) terephthalate is converted by polycondensation to PET, wherein ethylene glycol is produced again. A further production method of polyethylene terephthalate is the direct polycondensation of ethylene glycol and terephthalic acid at high temperatures while distilling off the resulting water.

Preferably, the second polymer layer (P2) has a smaller layer thickness than the polymer layer (P1). It is therefore preferred in the context of the present disclosure when the at least one second polymer layer (P2) has a layer thickness of from about 1.00 µm to about 100 µm, preferably from about 2.50 µm to about 50.0 µm, more preferably from about 5.00 µm to about 25.0 µm, in particular from about 10.0 µm to about 20.0 µm.

A particularly preferred product as contemplated herein is therefore exemplified in that multilayer film (F) comprises at least one second polymer layer (P2), which is formed from polyethylene terephthalate and has a layer thickness of from about 10.0 to about 20.0 µm.

The polymer layers (P1) and (P2) of the multilayer film (F) include organic polymeric materials, which usually have only an insufficient barrier effect with respect to gases and water vapor. When the oxidizing agent-containing composition is packaged in a package (VP) of a multilayer film (F), which comprises only the two organic polymer layers (P1) and (P2), water vapor can escape unhindered, so that the water content in the composition changes unacceptably during prolonged storage. In order to minimize the uncontrolled escape of water vapor from the package (VP), the organic polymer layers (P1) and (P2) are therefore used in conjunction with a barrier layer (BS).

The barrier layer (BS) has a passage barrier effect for gases and water vapor. As contemplated herein, it is meant that the barrier layer (BS) reduces the permeation rate of water vapor and gases through the film. A film (F) as contemplated herein, which has a barrier layer (BS) in addition to the layers (P1) and (P2), thus has with respect to a comparable film (with the same total thickness), which however only has the two layers (P1) and (P2) but has no barrier layer (BS), a reduced water vapor transmission and reduced gas permeability.

By way of example, the barrier layer (BS) is a thin layer which comprises an inorganic material, wherein the inorganic material can be applied to the organic polymer layer (P1) and/or (P2) with the aid of vacuum coating techniques (for example, PVD "physical vapor deposition" or CVD "chemical vapor deposition").

When the barrier layer (BS) is a layer which comprises at least one inorganic material, then, for example, aluminum, aluminum oxides, magnesium, magnesium oxides, silicon, silicon oxides, titanium, titanium oxides, tin, tin oxides, zirconium, zirconium oxide and/or or carbon can be considered. Particularly preferred in this context are oxides which can be selected from the group of aluminum oxides, magnesium oxides, silicon oxides, titanium oxides, tin oxides and/or zirconium oxides. In the context of the present disclosure, it is an aluminum layer that constitutes the barrier layer (BS).

The barrier layer (BS) of inorganic material is very particularly preferably between the two polymer layers (P1) and (P2). The production of films with barrier layers of inorganic material is described, for example, in document EP 1036813 A1, to which reference is made in full at this point.

The thicker the barrier layer (BS), the greater or stronger the passage barrier effect for gases and water vapor. The thickness of the barrier layer (BS) can therefore be chosen as a function of the desired barrier effect. The barrier layer (BS) can have, for example, a layer thickness of from about 1 to about 1000 nm (nanometers). The barrier layer (BS) preferably has a layer thickness of from about 5 to about 500 nm, more preferably of from about 10 to about 250 nm and particularly preferably of from about 10 to about 150 nm (nanometers). Preferred embodiments of the present disclosure are therefore exemplified in that the at least one barrier layer (BS) has a layer thickness of from about 1.00 nm to about 1000 nm, preferably from about 5.00 nm to about 500 nm, more preferably from about 10.0 nm to about 250 nm, in particular from about 10.0 nm to about 150 nm.

In addition to the previously described layers (P1), (P2) and (BS), the multilayer film (F) can additionally comprise one or more further layers. These further layers can be, for example, intermediate layers and/or adhesive layers. It is therefore preferred as contemplated herein when the at least one multilayer film (F) additionally contains at least one further layer selected from the group of intermediate layers (SZ), adhesive layers (SK) and mixtures thereof.

For example, the films (F) can have further intermediate layers (SZ) in order to increase the mechanical stability. Intermediate layers can also prevent or minimize the permeation of polymers or residual monomers from a polymer layer into the bleaching agent composition.

In addition, to increase the bond strength, the films can also comprise one or more adhesive layers (SK) to reduce or prevent delamination (that is, flaking or formation of air space) between two layers.

A particularly preferred product as contemplated herein is exemplified in that the multilayer film (F) additionally contains, in addition to the first polymer layer (P1), the second polymer layer (P2) and the barrier layer (BS), yet one or more further layers which are selected from intermediate layers (SZ) and/or adhesive layers (SK).

When the multilayer film (F) also contains yet further layers in addition to the layers (P1), (P2) and (BS), suitable arrangements as contemplated herein of the layers are described below (considered from interior (in contact with the bleaching agent composition) to the outside):

a) *Interior*-layer (P1)-first adhesive layer (SK1)-layer (P2)-second adhesive layer (SK2)-barrier layer (BS)-*outside*, b) *Interior*-layer (P1)-adhesive layer (SK1)-layer (P2)-barrier layer (BS)-*outside*, c) *Interior*-layer (P1)-layer (P2)-second adhesive layer (SK2)-barrier layer (BS)-*outside*, d) *Interior*-barrier layer (BS)-first adhesive layer (SK1)-layer (P1)-second adhesive layer (SK2)-layer (P2)-*outside*, e) *Interior*-barrier layer (BS)-adhesive layer (SK)-layer (P1)-layer (P2)-*outside*, f) *Interior*-barrier layer (BS)-layer (S1)-adhesive layer (SK)-layer (P2)-*outside*, g) *Interior*-layer (P1)-first adhesive layer (SK1)-barrier layer (BS)-second adhesive layer (SK2)-layer (P2)-*outside*, h) *Interior*-layer (P1)-adhesive layer (SK)-barrier layer (BS)-layer (P2)-*outside*, i) *Interior*-layer (P1)-barrier layer (BS)-adhesive layer (SK)-layer (P2)-*outside*

The problem underlying the present disclosure is further solved by the method of blonding human hair as contemplated herein. A second subject of the present disclosure is therefore a method for blonding human hair in which (a) the cosmetic agent according to the first aspect of the present disclosure is introduced into a quantity of water, (b) the resulting mixture of (a) is homogenized, and (c) the homogenized mixture of (b) is applied to the human hair.

As explained in detail above, the advantage of the present disclosure lies that a single packaged article is provided, the contents of which are added to water so that the bleaching agent composition is suspended and the homogenized mixture then constitutes a ready-to-use blonding composition. After application, the homogenized mixture is allowed to act and finally rinsed from the hair with water. Blonded hair is produced in this way.

The mixing ratio of bleaching agent composition to water according to a preferred embodiment of the present disclosure can be at from about 1:5 (about 1 part by weight of the agent as contemplated herein to about 3 parts by weight of water) to about 3:1, preferably at from about 1:2 to about 1:1.

The ready-to-use cosmetic agents of the cosmetic agent and water preferably have a viscosity in the range of from about 3000 to about 40,000 mPas, preferably from about 4000 to about 30,000 mPas, particularly preferably from about 6,000 to about 15,000 mPas, each measured at 20° C. with a Haake cylinder/cylinder Viscometer, turning/measuring system SV I with a cooling time of 5 minutes. The viscosity value is determined at a shear rate of 1/7.2 s in this measurement method. The measuring program works with the ramp of from 0-1/60 s. A viscosity in this range allows the ready-to-use cosmetic agent to be well applied on the one hand and have flowability on the other hand to ensure that the agent has a sufficiently long exposure time on the keratinic fibers at the site of action.

The exposure time after the above step c) is preferably from about 5 to about 60 minutes, in particular from about 5 to about 50 minutes, particularly preferably from about 10 to about 45 minutes. During the exposure time of the homogenized mixture on the hair, it can be advantageous to assist the color change process by supplying heat. An exposure phase at room temperature is also as contemplated herein. In particular, the temperature during the exposure time lies between about 20° C. and about 40° C., in particular between about 25° C. and about 38° C. The agents yield good treatment results even at physiologically compatible temperatures of below about 45° C.

After the end of the exposure, all components located on the keratin fibers are rinsed out of the hair with water or a surfactant-containing cleaning agent. Commercial shampoo in particular can be used as a cleaning agent in this case, wherein in particular the cleaning agent can then be dispensed with and the rinsing process can be done with tap water when the color changing agent has a higher surfactant content.

Features concerning preferred embodiments of the first subject of the present disclosure, which are described above only in this regard, of course, apply correspondingly to the second subject as features of preferred embodiments.

The following examples are intended to illustrate the subject matter of the present disclosure without limiting it in any way.

EXAMPLES

Formulations

The following formulations were prepared (unless stated otherwise, the amounts specified are % by weight)

Blonding Powder

|  | KM 1 | KM 2 |
| --- | --- | --- |
| Britesil C 265 | 22.4 | 27.0 |
| Magnesium carbonate (hard) | 30.8 | 2.6 |
| Carboxymethylcellulose (Cekol 50000) | 1.9 | 2.2 |
| Hydroxyethylcellulose (Tylose H 100000 YP 2) | 1.9 | 2.3 |
| Xanthan gum (Keltrol CG-SFT) | 2.4 | 3.7 |
| EDETA BX Powder | 1.6 | 1.6 |
| NaCl | 0.5 | 0.5 |
| Citric acid | 0.5 |  |
| L-arginine | 1.0 |  |
| Ammonium persulfate + 0.5% silica | 10.0 | 14.0 |
| Potassium persulfate | 19.0 | 27.4 |
| Sodium persulfate | 5.0 | 6.0 |
| Dimethicone/Dimethiconol | 3.0 | 2.4 |
| Sodium percarbonate | — | 10.0 |

The composition KM 1 is prepared as a two-chambered sachet, wherein 23 g of KM 1 are filled in the first chamber and about 2 g of percarbonate are filled in the second chamber.

The mixing ratio of the cosmetic agents with water is 1:2 in the case of the two-chamber sachet, wherein 50 g of water are used, and 1:3 in the case of the one-chamber sachet, wherein 75 g of water are used.

Furthermore, the following compositions were prepared:

Blonding Powder

|  | KM 3 | KM 4 | KM 5 |
| --- | --- | --- | --- |
| Magnesium carbonate (hard) | 12 | 22.8 | 2.6 |
| Britesil C 265 | 36.5 | 22.4 | 27 |
| Carboxymethylcellulose (Cekol 50000) | 2 | 1.9 | 2.2 |
| Hydroxyethylcellulose (Tylose H 100000 YP 2) | 2 | 1.9 | 2.3 |
| Xanthan gum (Keltrol CG-SFT) | 3.5 | 2.4 | 3.7 |
| EDETA BX Powder | 1.5 | 1.6 | 1.6 |
| Sodium persulfate | 5 | 5 | 6 |
| Ammonium persulfate + 0.5% silica | 14.5 | 10 | 14 |
| Potassium persulfate | 14.5 | 19 | 27.4 |

-continued

|  | KM 3 | KM 4 | KM 5 |
| --- | --- | --- | --- |
| Eumulgin B5 | 4.5 |  |  |
| NaCl | 0.5 | 0.5 | 0.5 |
| Dimethicone/Dimethiconol | 3 | 3 | 2.4 |
| Citric acid | 0.5 | 0.5 |  |
| L-arginine |  | 1 |  |
| Sodium percarbonate | 8 | 8 | 10 |
| Perfume |  |  | 0.3 |

Application

The formulations comprising KM 1 and KM 2 were provided for use.

The bag contents were mixed with lukewarm water and homogenized. The homogenized mixtures were applied to light brown Fischbach & Miller hair and left exposed for 45 minutes and then rinsed with tap water. Then the hair was dried.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic agent for blonding keratinic fibers, comprising
    (i) a package comprising at least one multilayer film, wherein the multilayer film comprises at least one layer comprising metal as a barrier layer, and
    (ii) a bleaching agent composition contained in the package, wherein the bleaching agent composition comprises:
        at least one percarbonate in a total amount of from about 2 to about 14% by weight based on the total weight of the bleaching agent composition and
        at least one inorganic salt of a peroxosulfuric acid, in a total amount of from about 10 to about 70% by weight based on the total weight of the bleaching agent composition,
        wherein the metal of the layer containing metal comprises aluminum.

2. The cosmetic agent according to claim 1, wherein the at least one inorganic salt of a peroxosulfuric acid is selected from the group of sodium peroxodisulfate, potassium peroxodisulfate, ammonium peroxodisulfate, sodium peroxomonosulfate, potassium peroxomonosulfate, ammonium peroxomonosulfate, or mixtures of these inorganic salts of a peroxosulfuric acid.

3. The cosmetic agent according to claim 1, wherein the inorganic salt of a peroxosulfuric acid includes a mixture comprising from about 5 to about 40% by weight of potassium peroxodisulfate, 5 to 20% by weight, from about 8 to about 18% by weight, of ammonium peroxodisulfate and from 0 to about 10% by weight of sodium peroxodisulfate, in each case based on the total weight of the blonding agent.

4. The cosmetic agent according to claim 1, wherein the at least one percarbonate constitutes an alkali metal, alkaline earth metal or ammonium salt of a percarbonate.

5. The cosmetic agent according to claim 1, wherein the multilayer film comprises at least one first polymer layer (P1), at least one second polymer layer (P2) and the barrier layer (BS), wherein the first polymer layer (P1) is formed from polyethylene terephthalate or polyethylene naphthalate; the second polymer layer (P2) is formed from a polyolefin; and/or the layer containing metal is formed from aluminum.

6. The cosmetic agent according to claim 5, wherein the barrier layer (BS) is arranged between the first polymer layer (P1) and the second polymer layer (P2).

7. The cosmetic agent according to claim 1, wherein the bleaching agent composition further comprises at least one thickening agent present in the bleaching agent composition in a total amount of from about 0.5 to about 15% by weight based on the total weight of the bleaching agent composition.

8. The cosmetic agent according to claim 1, wherein the at least one thickening agent is a mixture of a cellulose gum, a hydroxyethyl cellulose and a xanthan gum, wherein the amount of cellulose gum is from 0.2 to 5% by weight, the amount of xanthan gum is from 0.1 to 5% by weight, and the amount of hydroxyethyl cellulose is from 0.2 to 5% by weight, in each case based on the total weight of bleaching agent composition.

9. The cosmetic agent according to claim 1, wherein the bleaching agent composition comprises the at least one percarbonate in a total amount of from about 8 to about 10% by weight, based on the total weight of the bleaching agent composition.

10. The cosmetic agent according to claim 1, wherein the bleaching agent composition comprises the at least one inorganic salt of a peroxosulfuric acid in a total amount of from about 30 to about 50% by weight, based on the total weight of the bleaching agent composition.

11. The cosmetic agent according to claim 1, wherein the at least one inorganic salt of a peroxosulfuric acid comprises a mixture of potassium peroxodisulfate and ammonium peroxodisulfate, a mixture of sodium peroxodisulfate and ammonium peroxodisulfate, or a mixture of potassium peroxodisulfate ammonium peroxodisulfate, and sodium peroxodisulfate.

12. The cosmetic agent according to claim 1, wherein the inorganic salt of a peroxosulfuric acid includes a mixture comprising from about 10 to about 30% by weight of potassium peroxodisulfate, from about 10 to about 15% by weight of ammonium peroxodisulfate, and from about 2 to about 8.5% by weight of sodium peroxodisulfate, in each case based on the total weight of the blonding agent.

13. The cosmetic agent according to claim 1, wherein the multilayer film comprises at least one first polymer layer (P1), at least one second polymer layer (P2) and the barrier layer (BS), wherein the first polymer layer (P1) comprises polyethylene terephthalate; the second polymer layer (P2) comprises polyethylene; and the layer containing metal comprises aluminum.

14. The cosmetic agent according to claim 5, wherein the first polymer layer (P1) has a layer thickness of from about 5 to about 20 μm; the second polymer layer has a layer thickness of from about 50 to about 100 μm; and the layer containing metal has a layer thickness of from about 3 to about 30 μm.

15. The cosmetic agent according to claim 5, wherein the first polymer layer (P1) is located on a side facing away from the bleaching agent composition.

16. The cosmetic agent according to claim 1, wherein the package is a two-chamber bag and the percarbonate is contained in a first chamber of the two-chamber bag and the inorganic salt of a peroxosulfuric acid is contained in a second chamber of the two-chamber bag.

17. The cosmetic agent according to claim 1, wherein the multilayer film (F) has an oxygen transmission rate (OTR) of less than about 0.1 cc/m2/d/bar at about 23° C. and 0% relative humidity, and a water vapor transmission of less than about 0.1 g/m2d at about 38° C. and about 90% relative humidity.

18. A cosmetic agent for blonding keratinic fibers, comprising:
  (i) a package comprising at least one multilayer film, wherein the multilayer film comprises at least one layer comprising metal as a barrier layer, and
  (ii) a bleaching agent composition contained in the package, wherein the bleaching agent composition comprises:
    an alkali metal, alkaline earth metal or ammonium salt of a percarbonate in a total amount of from about 6 to about 12% by weight based on the total weight of the bleaching agent composition; and
    a mixture of potassium peroxodisulfate, ammonium peroxodisulfate, and sodium peroxodisulfate in a total amount of from about 30 to about 50% by weight based on the total weight of the bleaching agent composition;
  wherein the metal of the layer containing metal comprises aluminum.

19. The cosmetic agent according to claim 1, wherein the potassium peroxodisulfate is present in an amount of from about 10 to about 30% by weight, the ammonium peroxodisulfate is present in an amount of from about 10 to about 15% by weight, and the sodium peroxodisulfate is present in an amount of from about 2 to about 8.5% by weight, in each case based on the total weight of the blonding agent.

20. A method of blonding human hair in which
  (a) the cosmetic agent according to claim 1 is introduced into an amount of water,
  (b) the resulting mixture from (a) is homogenized, and
  (c) the mixture homogenized from (b) is applied to human hair.

* * * * *